United States Patent
Hassoon et al.

[11] Patent Number: 5,998,496
[45] Date of Patent: *Dec. 7, 1999

[54] PHOTOSENSITIVE INTRAMOLECULAR ELECTRON TRANSFER COMPOUNDS

[75] Inventors: Salah A. Hassoon; Ananda M. Sarker, both of Bowling Green; Douglas C. Neckers, Perrysburg, all of Ohio

[73] Assignee: Spectra Group Limited, Inc., Maumee, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/699,625

[22] Filed: Aug. 19, 1996

Related U.S. Application Data

[60] Provisional application No. 60/008,158, Oct. 31, 1995.

[51] Int. Cl.⁶ .................. C08F 4/52; C07F 5/02; C07F 5/06; C07F 5/00
[52] U.S. Cl. .................. 522/31; 522/35; 522/39; 522/40; 522/41; 522/42; 522/43; 522/44; 522/45; 522/46; 522/53; 522/63; 522/65; 522/66; 522/68; 522/904; 522/905; 522/182; 564/281; 564/282; 564/283; 568/2; 568/6; 568/7; 568/1
[58] Field of Search .................. 522/12, 14, 29, 522/26, 39, 46, 31, 35, 40, 41, 42, 43, 44, 45, 53, 65, 66, 68, 904, 905, 182; 568/1, 2, 7, 6; 564/281, 282, 283

[56] References Cited

U.S. PATENT DOCUMENTS

| | | | |
|---|---|---|---|
| 4,148,987 | 4/1979 | Winey | 526/316 |
| 4,481,276 | 11/1984 | Ishikawa et al. | 430/281 |
| 4,743,580 | 5/1988 | Kasamatsu et al. | 503/214 |
| 4,772,530 | 9/1988 | Gottschalk et al. | 430/138 |
| 4,772,541 | 9/1988 | Gottschalk et al. | 430/339 |
| 4,847,236 | 7/1989 | Satomura et al. | 503/208 |
| 4,859,572 | 8/1989 | Farid et al. | 430/281 |
| 4,902,604 | 2/1990 | Yamaguchi et al. | 430/281 |
| 4,948,819 | 8/1990 | Green et al. | 522/31 |
| 4,950,581 | 8/1990 | Koike et al. | 430/281 |
| 4,971,891 | 11/1990 | Kawamura et al. | 430/278 |
| 5,055,372 | 10/1991 | Shanklin et al. | 430/138 |
| 5,128,386 | 7/1992 | Rehmer et al. | 522/35 |
| 5,137,800 | 8/1992 | Neckers et al. | 430/281 |
| 5,395,862 | 3/1995 | Neckers et al. | 522/25 |
| 5,451,343 | 9/1995 | Neckers et al. | 252/582 |

FOREIGN PATENT DOCUMENTS

| | | |
|---|---|---|
| 0 281 941 | 9/1988 | European Pat. Off. ......... 522/905 |
| 0690074 | 1/1996 | European Pat. Off. . |
| 54-095687 | 7/1979 | Japan . |
| 54-151024 | 11/1979 | Japan . |
| 57-021401 | 2/1982 | Japan . |
| 58-040302 | 3/1983 | Japan . |
| 2020297 | 11/1979 | United Kingdom . |

OTHER PUBLICATIONS

Eaton, "Dye Sensitized Photopolymeriaztion" Advances in Photochemistry, vol. 13, pp. 427–488 (1986) John Wiley & Sons.

Chatterjie et al., "Electron Transfer Reactions in Cyanine Borate Ion Pairs; Photopolymerization Iniation Sensitive to Visible Light" JACS (1988), 110, pp. 2326–2328.

Chatterjie et al., "Photochemistry of Carbocyanine Alkyltriphenyl–borate Salts: Intra–Ion Pair Electron Transfer and the Chemistry of Boranyl Radicals" JACS (1990), 112, pp. 6329 to 6338.

Williams et al, Ketocoumarins as Photosensitizers and Photo–initiators, Polymer Eng. & Sci. vol. 23, No. 18, (1983).

Hassoon et al, "Electron Transfer Photoreduction of 5, 7, Diiodo–3–butoxy–3–fluorone with tetrabutylammonium triphenylbutyl–borate and N, N–Dimethyl–2, 6–diisopropylaniline", J. Phy. Chem (1995), 99, 9416–9424.

Hasoon et al, "Photochemistry of Benzophenonemethylri–n–butylammonium Tripenylbutylborate: Inter and Intra Ion–Pair Electron Transfer Photoreduction" JACS 117, 11369 (1995).

Primary Examiner—Susan W. Berman
Attorney, Agent, or Firm—Thompson Hine & Flory LLP

[57] ABSTRACT

A compound of the general formula:

$$A-L^+D^-$$

where A is a moiety which absorbs radiation and enters an excited state in which it accepts an electron; $D^-$ is a moiety which donates an electron to the excited state A and releases a free radical; and $L^+$ is a cationic linking group which tethers electron acceptor moiety A to electron donor moiety $D^-$. Cationic linking moiety $L^+$ has the formula:

$$-L'-G-$$

where L' is a moiety which forms a stable radical with acceptor moiety A upon transfer of an electron from donor moiety $D^-$ to electron acceptor moiety A, and G is a moiety which forms a leaving group upon transfer of the electron from donor moiety $D^-$ to acceptor moiety A.

20 Claims, No Drawings

PHOTOSENSITIVE INTRAMOLECULAR ELECTRON TRANSFER COMPOUNDS

This application claims priority from U.S. Provisional Application No. 60/008,158 filed Oct. 31, 1995.

BACKGROUND OF THE INVENTION

The present invention relates to photosensitive boranyl compounds and related compounds which generate active species (free radicals, organic bases, Lewis acids) when exposed to radiation.

Carbocyanine alkyltriphenylborate salts have proven effective visible light sensitive photoinitiators for rapidly polymerizing polyolacrylate monomer systems as described in U.S. Pat. Nos. 4,772,541 and 4,772,530 to Gottschalk, et al.; U.S. Pat. No. 4,859,572 to Farid, et al.; U.S. Pat. No. 4,847,236 to Satomura, et al.; U.S. Pat. No. 4,902,604 to Yamaguchi, et al.; U.S. Pat. No. 4,950,581 to Koike, et al; U.S. Pat. No. 4,971,891 to Kawamura, et al.; and U.S. Pat. No. 5,055,372 to Shanklin, et al.

It has been shown that the photoreactions of carbocyanine alkyltriphenylborate salts involve an electron transfer from the borate to the singlet state of the cyanine cation by Chatterjee, et al., in J. Am. Chem. Soc. 1988,110,2326 and J. Am. Chem. Soc. 1990,112,6329. Because the lifetime of the cyanine singlet is short (pico seconds), the electron transfer is observed only in nonpolar solvents where the transfer can occur from the tight ion pair. It has been reported by Hassoon et al., J. Phys. chem. 1995, 99, 9473 that photoreduction of fluorone dyes by triphenylbutyl borate salts is useful for the initiation of free radical polymerization, and that intermolecular electron transfer from the borate anion to the triplet state of the dye leads to the formation of butyl radicals which initiate polymerization.

As disclosed by Farid et al., in U.S. Pat. No. 4,959,572, activators are recognized in the art to fall into two distinct classes. One class of activators is referred to as electron acceptor activators. These activators liberate a free radical capable of initiating ethylenic addition by accepting an electron from a photosensitizer in its excited state. The reactions can be diagramed as follows:

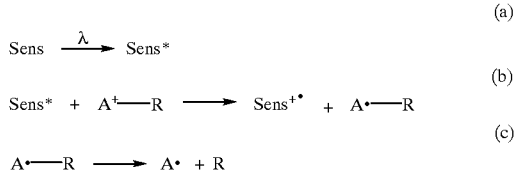

where
- Sens represents a photosensitizer,
- λ represents exposure to actinic radiation,
- * indicates the excited state produced by light absorption on exposure,
- $A^+$-R represents the electron acceptor activator,
- $A^+$ represents the electron accepting moiety of the activator before an electron is accepted,
- A represents the electron accepting moiety of the activator after an electron is accepted,
- R represents the moiety that is ultimately cleaved as a free radical,
- $Sens^{+\bullet}$ shows the photosensitizer converted to a cation radical by loss of an electron, and • denotes a radical.

Another class of activators is referred to as electron donor activators. These activators are oxidized by donating an electron to the excited state of the photosensitizer, thus liberating a free radical capable of initiating ethylenic addition. The reactions can be diagrammed as follows:

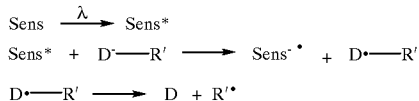

where
- $D^-$-R' represents the electron donor activator,
- $D^-$ represents the electron donating moiety of the activator before donating an electron,
- D represents the electron donating moiety of the activator after donating an electron,
- $Sens^-$ shows the photosensitizer converted to an anion by loss of an electron, and the retaining symbols are as indicated above.

A survey of electron acceptor and electron donor activators useful with photosensitizers is set forth in Volman et al., Advances in Photochemistry, Vol. 13, in the chapter titled "Dye Sensitized Photopolymerization" by D. F. Eaton, pp. 427 to 488, John Wiley & Sons (1986).

Specht and Farid in published U.K. Specification No. 3,083,832A disclose photopolymerization coinitiators including an azinium electron acceptor activator and acting as a photosensitizer, an amino-substituted ketocoumarin.

Gottschalk et al in published European Patent Application No. 0223 587 disclose a polymerization system including as an initiator a zwitterion consisting of an undissociated borate anion and a dye cation. Disclosed cationic dyes include Methylene Blue, Safranine O, Malachite Green, and various cyanine and rhodamine dyes. For example, U.S. Pat. Nos. 4,772,541 4,772,530 and 5,055,372 all to the Mead Corporation; U.S. Pat No. 4,859,572 to Eastman Kodak corporation; and U.S. Pat. Nos. 4,859,236, 4,902,604 and 4,950,581 to Fuji Photo Film Co., Ltd. teach that carbocyanine alkyltriphenylborate salts have proven to be effective visible light sensitive photoinitiators which rapidly polymerize polyolacrylate monomer systems.

European Patent Application No. O 690 074 A1 to Toyo Ink Manufacturing Co., Ltd. published Jan. 3, 1996 discloses a photopolymerization initiator composition containing (A) a sulfonium organoboron complex or oxosulfonium organoboron complex; and (B) a sensitizer which has electron donating capability and electron acceptability in an excited state. Aromatic ketones not linked to the borate via a cationic linking group are disclosed as being sensitizers. Japanese Kokai Tokyo Koho JP 08 03210 discloses organosulfonium borates as initiators for polymerization of unsaturated compounds upon irradiation by light or heating.

SUMMARY OF THE INVENTION

This invention is more particularly directed to redox reactions in which alkylaryl borates are the electron donors and aromatic ketones or coumarins are the electron acceptors. In particular, Benzophenone ammonium salts are provided where complexation of an electron donor such as a borate anion to the electron accepting benzophenone permits electron transfer to the triplet state of the benzophenone.

The present invention provides novel photosensitive compounds which are represented by the formulas (I), (II) or (III):

$$A-L-D \qquad (I)$$

where A is a moiety which absorbs radiation and enters an excited state which accepts an electron, L is a linking group which tethers the electron acceptor moiety A to the electron donor moiety D, and D is a moiety which donates an electron to the excited state of the A moiety and releases a free radical; and $$A-L^+D^- \qquad (II)$$

where A and D are defined as above and $L^+$ is a linking leaving group which ionically links the anionic electron donor moiety $D^-$ to the electron acceptor moiety A.

The linking group L is preferably a group of the formula $-L'-G$ where $-L'-$ as defined below is a moiety which yields a stable radical upon electron transfer and G is a good leaving group. Typically G is an ammonium, e.g., a quaternary ammonium group. Other examples of G include phosphonium, arsonium, antimonium, sulfonium, oxonium, thioxonium, halonium or polyvalent metal cation. One example of compounds of the formula (II) is compounds of the formula (IIA)

$$A \!-\!\!\left[L'\right]\!\!-\!\!N^+R_3D^- \qquad (IIA)$$

where L' is a moiety selected from the group consisting of $-CH_2-$, $$-\underset{\underset{CH_2CH_3}{|}}{\overset{\overset{CH_2\varnothing}{|}}{C}}-$$

$-O-$, $-S-$, and the like; R is the same or different and represents hydrogen, alkyl, aryl, arylalkyl or a high molecular weight moiety such as a poly- or copolyacrylate, a poly- or copolymethacrylate, a novolak resin, a poly- or copolystyrene, and the like; and A and D are defined as above. R will be selected to provide the solubility desired in the compounds of formula (IIA) or other properties desired in the compound such as solubility in a solvent for photoresist spinning or adhesion to a support.

In another embodiment, the invention provides polymers and copolymers having a repeating unit of the formula (III):

$$\begin{array}{c}(M)_n\\|\\N^+R^1_2D^-\\|\\L'-A\end{array} \qquad (III)$$

where M is a moiety derived from polymerization of one or more monomers; $R^1$ is hydrogen or an alkyl group having 1 to 6 carbon atoms; n is more than 10; preferably between 10 and 20, but can be higher; and A, D and L' are defined as above.

The higher molecular weight moiety R in formula (IIA) or the moiety M in formula (III) can be the product of the polymerization of a functionalized acrylate, methacrylate, or styrene of the formula:

$$CH_2=CR^2EWG$$

where $R^2$ is hydrogen or methyl, EWG is an electron withdrawing group such as $COOR^3$, $CONR_2^3$, CN, $P(O)OR_2^3$, $COR^3$, $C(O)OCOR^3$, $NO_2$, NCS, NCO, $SO_2R^3$, $SO_3R^3$, $SO_2NR_2^3$, $CX_3$, and the like where $R^3$ is hydrogen, $C_1-C_6$ alkyl or phenyl and X is halogen such as chlorine. More generally, M or R in formula III is the product of the polymerization of a functionalized acrylate, methacrylate, acrylamide or methacrylamide of the formula:

$$CH_2=CR^2COR^4$$

where $R^2$ is hydrogen or methyl and $R^4$ is hydroxy, alkoxy or a dialkylaminoalkoxy group in which the alkyl moieties may have 1 to 6 carbon atoms and the alkoxy moiety may have 1 to 10 carbon atoms or R is a dialkylamino group in which the alkyl moieties may have 1 to 6 carbon atoms. Other polymers and monomers to be included as R in formula IIA or M in formula III are the functionalized styrenics, $PhC(R^2)=CR_2^3$ where $R^2$ is H or $CH_3$; $R^3$ is H; and Ph is a phenyl group or a phenyl group substituted by $R^5$, or $OR^6$, $R^5$ is alkyl, aryl, aralkyl, alkaryl, alkenyl, alkynyl, alicyclic or heterocyclic groups and $R^6$ is H, alkyl, aryl, aralkyl, alkaryl, alkenyl, alkynyl, alicyclic or heterocyclic groups.

In one aspect of the invention, the photosensitive compounds are useful as photoinitiators in the photopolymerization of ethylenically unsaturated compounds such as acrylates, methacrylates and the like.

Compounds of the formula (III) are useful in photoimaging systems, such as photoresists, wherein the photosensitive compounds, upon irradiation, liberate polymeric amines in the exposed areas that can anionically cure epoxy resins. This will be recognized as a negative imaging system. The polymeric amines being basic also have a different solubility in an acidic solution than the unreacted photosensitive compound of formula (III) in the unexposed areas, which allows the image to be developed by selective dissolution and removal of the amine in aqueous acid followed by water and solvent wash. This will be recognized as a positive imaging system. In this mode, these resins are particularly useful in forming polymeric resist images on substrates that are base-sensitive such as porous luminescent silicon and other substrates used in semi-conductor technology.

DETAILED DESCRIPTION OF THE INVENTION

In accordance with the present invention, the electron accepting moiety absorbs radiation and accepts an electron in an excited state from the electron donor moiety which then releases a free radical. The structure of the pre,sent compound is such that the electron acceptor moiety is tethered to the electron donating moiety by a linking group in which case the electron transfer is believed to proceed via an intramolecular mechanism.

The electron acceptor moiety represented by A in the above formula can be derived from any of a wide range of absorbers known in the art by reaction with a linking group. One of the most common classes of absorbers which become acceptors (A) in their excited states are aromatic ketones, e.g., benzophenones; xanthanones; thioxanthones; oximinoketones; quinones; acetophenone acetals sold by Ciba- Geigy under the tradename Irgacures; acetophenone acetals sold by Merck under the tradename DAROCURE; keto dyes; cyanine dyes; merocyanine dyes; merostyryl dyes; oxonal dyes; xanthene dyes; hemioxonal dyes; acetophenone acetals; benzoin ethers; polycyclic aromatic hydrocarbons; halonium salts, such as iodonium salts; sulfonium salts; and the like. Preferably, the acceptor moiety A is an aromatic ketone such as benzophenone, substituted benzophenones, acetophenone, substituted acetophenones, or a coumarin such as coumarin, and substituted coumarins.

Examples of substituted benzophenones are:

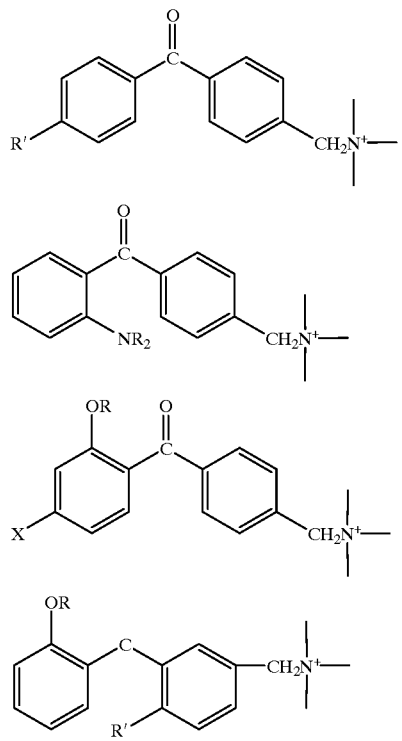

X = Br, Cl
R' = CH₃, ———OH, ———OR (R = alkyl or aryl)

Examples of substituted coumarins are:

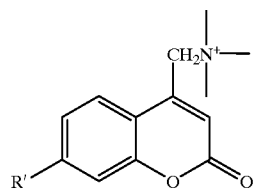

R' = NR₂ or OR, where R is any alkyl group

Most preferably, the aromatic ketone is benzophenone.

Other examples of absorbers useful in the invention are described in U.S. Pat. No. 3,652,275 (chalcone type or dibenzylacetone type compounds); U.K. Patent No. 2,020, 297 (merocyanine compounds); Japanese Patent Unexamined Publication (hereafter referred to as "KOKAI") No. Sho 58-40302 (thiopyrylium salts); KOKAI No. Sho 57-21401 (dialkylamino-stilbene compounds); and in KOKAI Nos. Sho 54-95687 and Sho 54-151024 and U.S. Pat. No. 4,481, 276 (merocyanine compounds). Moreover, ketocoumarin is used as a light absorber and N-phenyl glycine is used as an activator in "Polymer Engineering and Science," 1983, p. 1022.

Other examples of light absorbers are disclosed by D. F. Eaton in "Advances in Photochemistry," 1987, 13, pp. 427–488. Specific examples of the light absorbers are acridinium dyes such as acriflavine; xanthene dyes such as Rose Bengal and thiazine dyes such as Thionine and Methylene Blue, and specific examples of the activators are amines such as triethanolamine, hydrazine and triphenylamine; phosphorus compounds such as triphenyl phosphine and tri-n-butyl phosphine; sulfinic acids such as sodium p-tolune-sulfinate; sulfonic acid esters such as methyl-toluene-sulfonate; heterocyclic compounds such as oxazole and imidazole; enolate compounds such as dimedone; tin compounds such as tributylbenzyl tin; arylthiourea and N-phenyl glycine.

Additional examples of light absorbers are disclosed in U.S. Pat. No. 4,743,580 which is incorporated herein by reference to the extent necessary to disclose representative light absorbers and activators.

In accordance with the invention, the absorber moiety is modified to include a linking moiety L which can covalently or ionically tether the absorber moiety A to a donor moiety. The chemistry used to introduce the linking group will vary with the nature of the absorber.

When benzophenones are the absorber, the linker moiety is a cation attached to the benzophenone ring via a methylene group as shown in Scheme I below. Electron transfer from borate anion to benzophenone triplet state (BP*³) gives (4) and boranyl radicals both of which dissociate rapidly. Radical (4) dissociates to give (5) and the amino cation radical followed by second electron transfer ($k_{bet}$) to give tributylamine and BPCH₂. radical (6). The latter is stable and couples either with a similar radical to produce (7), or to the butyl radical to produce (8). Both products were separated and identified.

Scheme 1

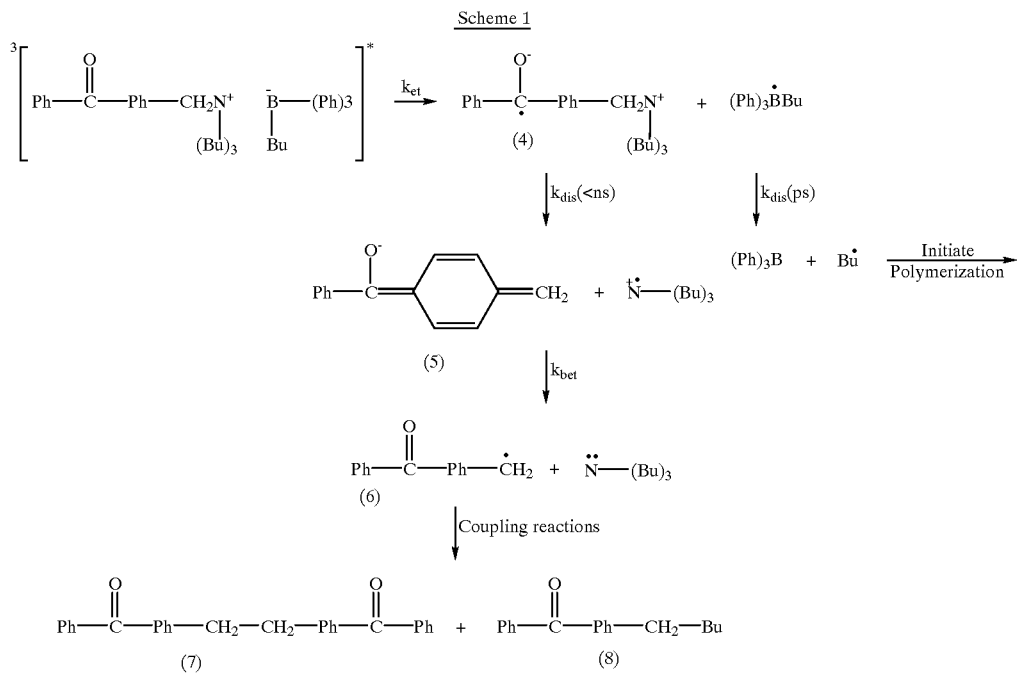

When fluorones or xanthones are the absorber, the linking group may be attached at specific sites such as those with oxygen (C-3 and C-6) or I(C-2,4,5, or 7). For example, the linker $R^7$ is acetyl in the xanthene, rose bengal (RB), hereafter referred to as RBAX.

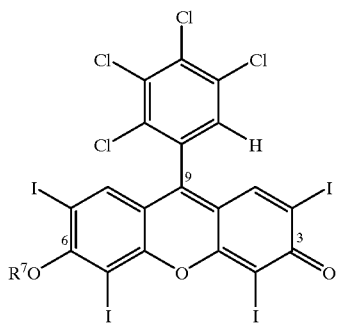

The photoreduction of RBAX by triphenyl n-butyl borate ion (BO⁻) takes place in ethyl acetate according to the following:

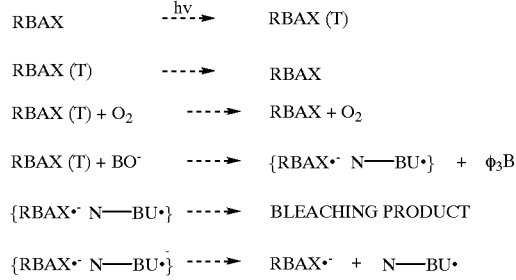

In the case of the Irgacures, the linking chemistry is similar to that with benzophenones. The example shown is with Irgacure 369. The linker is $-N^+(CH_3)_3$. The photochemistry proceeds as follows:

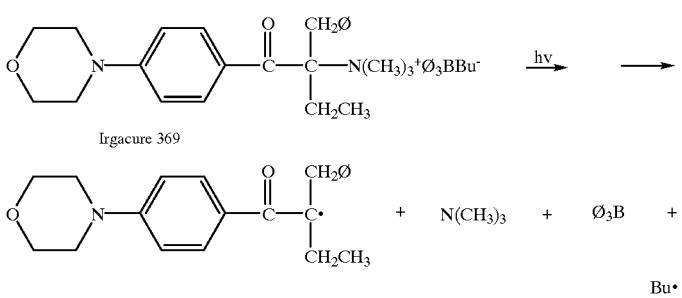

Those skilled in the art will be able to identify suitable chemistries to introduce linking groups onto other absorbers.

The electron donor moiety D, which donates an electron to the excited state of the electron acceptor moiety, is represented by the formula (V):

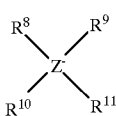

(V)

where Z is an element selected from the groups III A or IV A of the Periodic Table and $R^8$, $R^9$, $R^{10}$ and $R^{11}$ are independently selected from the group consisting of alkyl, aryl, aralkyl, alkaryl, alkenyl, alkynyl, alicyclic heterocyclic and a cyclic group, wherein at least two of the $R^8$, $R^9$, $R^{10}$ and $R^{11}$ may combine to form a cyclic group.

Preferably, the electron donor is a borate, aluminate or gallate and, most preferably, it is a borate such as tetralkylborate, tetraarylborate, triarylalkylborate, dialkyldiarylborate or aryltrialkylborate. In a particularly preferred aspect of the invention, the electron donor moiety is triarylalkylborate and, most preferably, it is a triphenylbutylborate.

Where the donor moiety is ionically bonded to the linking group, complexation can be accomplished by choosing a positive ion ($M^+$) such as ammonium, phosphonium, arsonium, antimonium, sulfonium, oxonium, thioxonium, halonium or polyvalent metal cation. The general structure is:

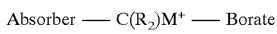

For covalent bonding of the linking group to the donor, a carbon boron bond may be used to form a compound as in formula IV:

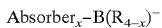

(IV)

Where X is 1 to 4. Direct irradiation of such compounds leads to formation of an alkyl radical (R) thus suggesting an intramolecular redox reaction similar to those in the complexed systems. A specific example is that of the benzo(B) thiophene borate (complexing ammonium ion not shown) below:

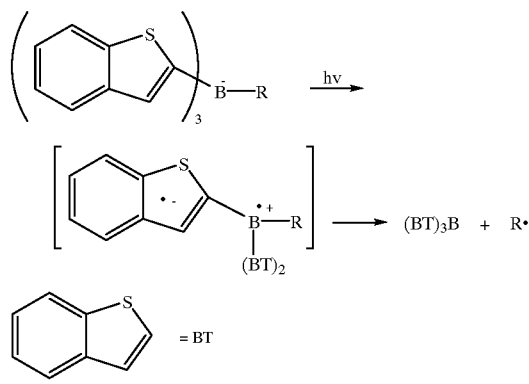

This compound is prepared by the following procedures:

EXAMPLE 1

Tetramethylammonium-Tri-2 benzo[b] thienylcyclopentylborate.

Step 1. A dry, 50 mL round-bottomed flask equipped with a magnetic stirrer and a silicone rubber septum was flushed with argon and cooled in an ice bath and charged with solution of 0.3 mL of cyclopentene (3.4 mmol) in 15 mL of pentane. The mixture was stirred and maintained at 0° C. A solution of $BCl_3$ (1 m in heptane) 2.7 mL (2.7 mmol) was added followed by slow addition of 0.31 mL of $BHCl_2.Me_2S$ (2.7 mmol). The mixture was stirred for 1 h at 25° C. and the solvent was then removed via a syringe to leave solid precipitate of trichloroborane-dimethyl sulfide.

Step 2. A dry 100 mL round-bottomed flask equipped with a mechanical stirrer, a reflux condenser, a low temperature thermometer and a silicone rubber septum was flushed with argon. 2-benzo[B]thienyllithium was prepared in situ from 1.1 g of benzo[B]thiophene (8.21 mmol) and 3.3 mL of 2.5 m solution of n-BuLi (in hexanes) in 20 mL of ether. The mixture was cooled to −90° C. and the solution of dichlorocyclopentylborane obtained in step 1 was added over 10 min while stirring was maintained. The mixture was brought to 20° C. and stirred for 2 h at this temperature. Distilled water (20 mL) was added with vigorous stirring. The top layer formed was separated and discarded. The aqueous layer was poured into 30 mL of saturated solution of $NME_4CL$ and shaken. The precipitate formed was filtered, washed with 60 ml of distilled water, and recrystallized from acetone/methanol=3/2 yielding 1.2 g (79%) of white crystalline solid. m.p. 234–236° C. $^1H$ NMR ($D_6$-DMSO, 200 MHz) δ 7.69 (d, J=7.6 Hz, 3H), 7.57 (d, J=7.6 Hz, 3H), 7.14 (t, J=7.4 Hz, 3H), 7.07 (s, 3H), 7.04 (t, J=7.4 Hz, 3H), 3.04 (s, 12H), 1.85 (m, 2H), 1.65 (m, 1H), 1.37 (br s, 6H). $^{13}C$ NMR ($D_6$-DMSO, 50 MHz) δ 141.9, 124.1, 122.5, 121.4, 120.9, 54.51 (t, J=4 HZ), 31.38, 27.34. $^{11}B$ NMR (DMSO, 128 MHz) δ −30.36. Anal. Calcd. for $C_{33}H_{36}BNS_3$: C, 71.59; H, 6.55; N, 2.53; S, 17.37. Found: C, 71.50; H, 6.63; N, 2.53; S, 17.30.

EXAMPLE 2

Tetramethylammoniumtri-2-benzo[b]thienyl-2-phenylethylborate. Prepared by substituting dichloro-2-phenylethylborane for dichlorocyclopentylborane in the method of Example 1. White solid. m.p.>270° C. $^1H$ NMR ($D_6$-DMSO, 200 MHz) δ 7.72 (d, J=7.4 Hz, 3H), 7.61 (d, J=7.4 Hz, 3H), 7.16 (m, 10H), 7.06 (m, 4H), 3.04 (s, 12H), 2.53 (m, 2H), 1.40 (m, 2H). $^{13}C$ NMR ($D_6$-DMSO, 50 MHz) δ 148.8, 142.2, 141.9, 128.1, 127.9, 124.5, 123.6, 122.7, 121.5, 121.1, 54.52 (t, J=3.9 Hz), 34.61. $^{11}B$ NMR (DMSO, 128 MHz) δ −31.74. Anal. Calcd. for $C_{36}H_{36}BNS_3$: C, 73.32; H, 6.15; N, 2.37; S, 16.31. Found: C, 73.12; H, 6.17; N, 2.36; S, 16.38.

EXAMPLE 3

Tetramethylammoniumtri-2-benzo[b]thienyl-2-(p-chloro) phenylethylborate. Prepared by substituting dichloro-2-p-chlorophenylethylborane for dichlorocyclopentylborane in the method of Example 1. Pale yellow solid. m.p. 158° C. (decomp.). $^1H$ NMR ($D_6DMSO$, 200 MHz) δ 7.71 (d, J=7.6 Hz, 3H), 7.59 (d, J=7 Hz, 3H), 7.11 (m, 13H), 3.06 (s, 12H), 2.53 (m, 2H), 1.30 (m, 2H). $^{13}C$ NMR ($D_6DMSO$, 50 MHz) δ 147.7, 142.2, 141.9, 129.7, 129.0, 128.0, 123.65, 122.7, 121.6, 121.2, 54.52 (t, J=4 Hz), 33,99. $^{11}B$ NMR (DMSO, 128 MHz) δ −31.79. Anal. Calcd. for $C_{36}H_{35}BClNS_3$: C, 69.28; H, 5.65; Cl, 5.68; N, 2.24; S, 15.41. Found: C, 69.09; H, 5.70; Cl, 5.74; N, 2.18; S, 15.46.

EXAMPLE 4

Tetramethylammoniumtri-2-benzo[b]thienyl-2-methylcyclohexylborate. Prepared by substituting dichloro-2-methylcyclohexylborane for dichlorocyclopentylborane in the method of Example 1. The compound was obtained as stable complex (1:0.62 molar ratio) with acetone. White solid. m.p.>270° C. IR (KBR pellet): 3049, 2978, 2909, 2840, 2782, 1710 (acetone C=O), 1479, 1450, 1420, 1288, 946, 749, 728, 712. $^1$H NMR ($D_6$-DMSO, 200 MHz) δ 7.68 (d, J=7.6 Hz, 3H), 7.57 (d, J=7.6 Hz, 3H), 7.27 (s, 3H), 7.12 (t, J=6.4 Hz, 3H), 7.02 (t, J=6.4 Hz, 3H), 3.05 (s, 12H), 2.08 (s, 3.72H acetone), 1.89 (m, 1H), 1.58 (m, 2H), 1.44 (m, 1H), 1.07 (br s, 6H), 0.77 (br s, 3H). $^{11}$B NMR (DMSO, 128 MHz) δ -29.54 Anal. Calcd. for $C_{35}H_{40}BNS_3 \cdot 0.62\ C_3H_6O$: C, 73.32; H, 6.15; N, 2.37; S, 16.31. Found: C, 73.12; H, 6.17; N, 2.36; S, 16.38.

EXAMPLE 5

Tetramethylammoniumtri-2-benzo[b]thienyl-2-(2,3-dimethyl)butylborate. Prepared by substituting dichloro-2,3-dimethylbutylborane for dichlorocyclopentylborane in Example 1. Yellow solid. m.p. 257–258° C. (from acetone/methanol 1/1). IR (KBR pellet) : $^1$H NMR ($D_6$-DMSO, 200 MHz) δ 7.68 (d, J=7.4 Hz, 3H), 7.57 (d, J=7.2 Hz, 3H), 7.19 (s, 3H), 7.08 (m, 6H), 3.04 (s, 12H), 2.13 (quintet, J=7 Hz, 1H), 1.09 (s, 6H), 0.69 (d, J=7 Hz, 6H). $^{13}$C NMR ($D_6$-DMSO, 50 MHz) δ 141.9, 141.7, 125.8, 122.4, 121.4, 121.1, 121.0, 54.51 (t, J=4 Hz), 35.01, 25.18, 20.63. $^{11}$B NMR (DMSO, 128 MHz) δ -27.09 Anal. Calcd. for $C_{35}H_{40}BNS_3$: C, 71.68; H, 7.08; N, 2.46; S, 16.88. Found: C, 71.66; H, 7.04; N, 2.52; S, 16.94.

The irradiation of a 0.01M solution of tetramethylammoniumtri-2-benzo[b]thienyl-2-(2,3-dimethyl)butylborate also containing 5 equivalents of methyl acrylate with 300 nm light in a Rayonet reactor, at room temperature, under Argon, leads to the formation of 2,3-dimethyl-2-butyl radicals. The addition of this radical to methyl acrylate provides methyl 4,4,5-trimethylhexanoate (49% yield). The byproduct is benzo[b]thiophene.

Examples of compounds in accordance with the invention are shown in Table I and Table IA.

TABLE I

| COMPOUND |
|---|
| $Ph_3B^-$—Bu $(C_4H_9)_3N^+$—$CH_2$Naphthalene |
| $Ph_3B^-$—Bu $(C_4H_9)_3N^+$—$CH_2$—Ph—CO—Ph |
| $Ph_3Ga^-$Bu $(C_4H_9)_3N^+$—$CH_2$—Ph—CO—Ph |
| $sBu_3B^-$Ph $Me_3N^+$Ph—CO—Ph—$NMe_2$ |
| $Ph_3B^-$—Bu $Me_3N^+$Ph—CO—Ph—$NMe_2$ |
| $Ph_3B^-$—Bu Ph—$I^+$—Ph |
| $Ph_3B^-$—Bu Ph—$I^+$—Ph—$OC_6H_{13}$ |
| $H_2C$=$C(Me)CO_2$—$CH_2$—$CH_2$—$N^+(Me)_2$—$CH_2$—Ph—CO—Ph |
| $Ph_3B^-$Bu |

TABLE IA

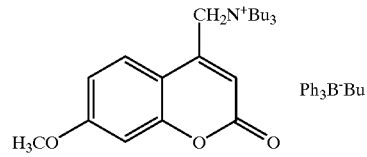

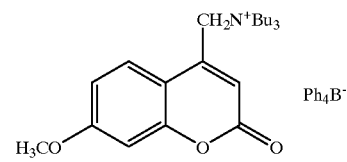

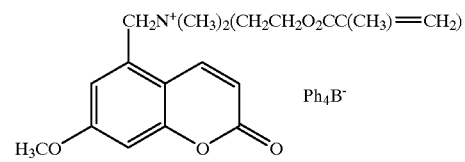

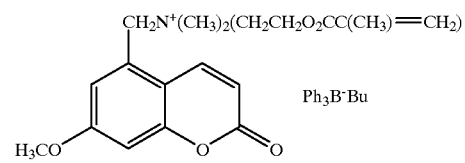

TABLE IA-continued

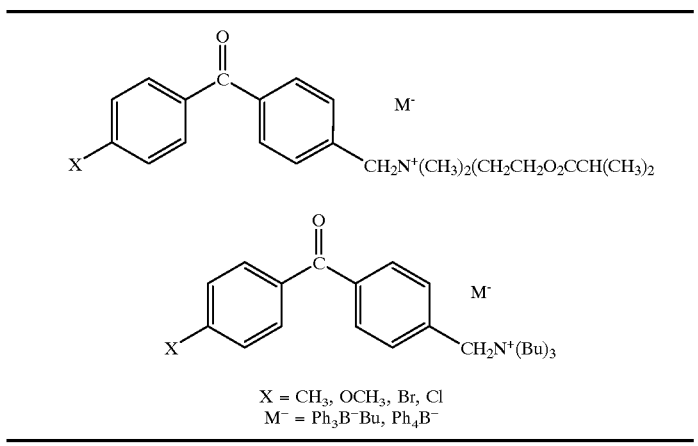

X = CH₃, OCH₃, Br, Cl
M⁻ = Ph₃B⁻Bu, Ph₄B⁻

In a particularly preferred embodiment of the present invention, the compounds of choice are N,N,N-tributyl-N-(p-benzoyl)benzyl ammonium triphenylbutyl borate, pyrenetriethylammonium triphenylbutylborate, N,N,N-tributyl-N-(p-benzoyl)benzyl ammonium tetraphenyl borate, 7-alkoxy-4-methylammonium coumarin triphenylbutylborate and 7-alkoxy-4-methylammonium coumarin tetraphenylborate.

Typical examples of compounds which can be photopolymerized using compounds of the formula I and II are ethylenically unsaturated compounds and, more specifically, polyunsaturated compounds. These compounds include both monomers having one or more ethylenically unsaturated groups, such as vinyl or allyl groups, and polymers having terminal or pendant ethylenic unsaturation. Such compounds are well known in the art and include acrylic and methacrylic esters of polyhydric alcohols such as trimethylolpropane, pentaerythritol, and the like; and acrylate or methacylate terminated epoxy resins, acrylate or methacrylate terminated polyesters, etc. Representative examples include ethylene glycol diacrylate, ethylene glycol dimethacrylate, trimethylolpropane triacrylate (TMPTA), pentaerythritol tetraacrylate, pentaerythritol tetramethacrylate, dipentaerythritol hydroxpentacrylate (DPHPA), hexanediol-1,6-dimethacrylate, and diethyleneglycol dimethacrylate.

When employed in a photosensitive composition for the polymerization of a photopolymerizable compound, the compound of the present invention is usually used in an amount up to about 1% based on the weight of the photopolymerizable compound. More typically, the compound is used in an amount of about 0.01 to 1% by weight and most typically about 0.2%.

While the compounds of this invention can be employed alone as the initiator in photopolymerizable compositions, the use of other conventional initiators and coinitiators in conjunction with the present compounds may be beneficial. Such additional initiator and coinitiators are well known in the arts and are disclosed in commonly owned U.S. Pat. No 5,451,343.

In another manifestation of the present invention the compounds are polymers of the formula III, including a repeating unit such as that in (9), Scheme 2. These polymeric compounds may be used in photoimaging systems which produce three-dimensional relief images on a substrate distinguishable in the light-exposed and the unexposed areas. Upon exposure to radiation preferably at about 365 nm, the polymer exhibits differential solubility in a developing solvent in the exposed and unexposed areas wherein the more soluble material is removed from the substrate. For example, the material in the exposed areas are removed from the substrate with aqueous hydrochloric acid. Remaining nonbasic organic material is then removed by an ethanol wash to produce a positive-tone relief image.

Tertiary amines are known in the art of thermal epoxy crosslinking. In another manifestation of the present invention the compounds of formula III photogenerating polymeric amine (10), Scheme 2, can be used as curing agents for thermal induced epoxy crosslinking and the latter utilized in both microlithography and coatings/adhesives technology. Photoresist film is spinned from the two component solution containing polymer (9) and an epoxy resin with a terminal epoxide group. Upon exposure to radiation preferably at 365 nm and subsequent thermal exposure at 80° C. for 30 min, the polymer film exhibits differential solubility in developing solvent (acetonitrile) in the exposed and unexposed areas. Thus, noncrosslinked material from unexposed areas can be easily removed leaving the exposed areas in tact after development. The outlined process sequence leads to the formation of the negative-tone relief image.

For poly 2-[N,N-dimethyl,N-(p-benzoyl)benzylammonium(triphenyl-n-butylborate)]ethyl methacrylate, upon UV radiation at 365 nm, rapid quenching of the excited state via single electron transfer (SET) from the triphenyl-n-butylborate anion and subsequent reactions lead to the formation of polymeric amine (10). The total reaction is illustrated in Scheme 2. The liberation of the target polymer with its pendant dimethylamino functionality is accompanied by the formation of biphenyl (from the triphenylboron) and products of the coupling of p-benzoylbenzyl radical (with itself and with the n-butyl radical).

Scheme 2

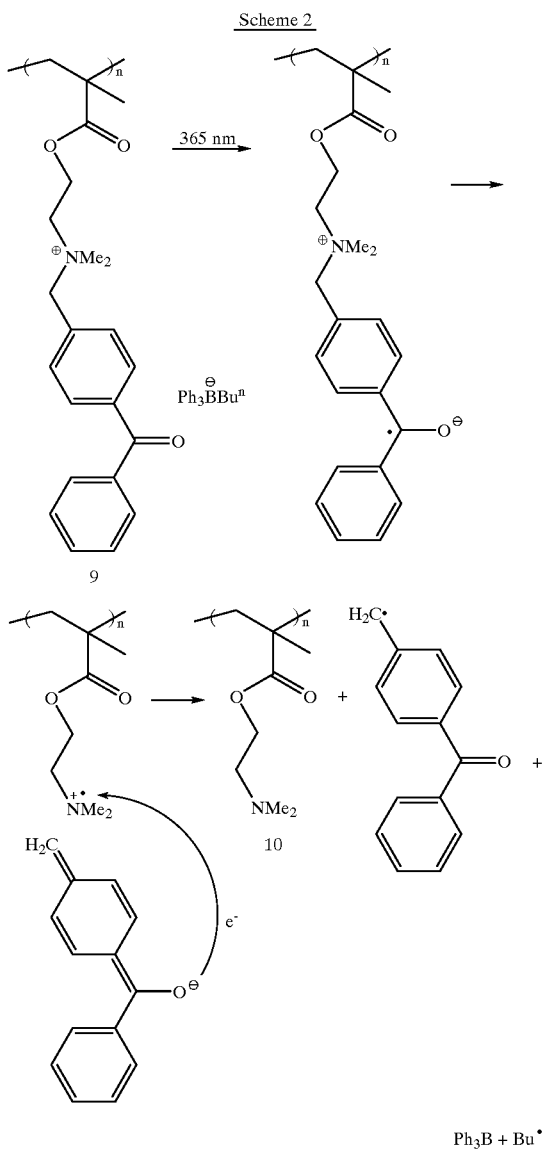

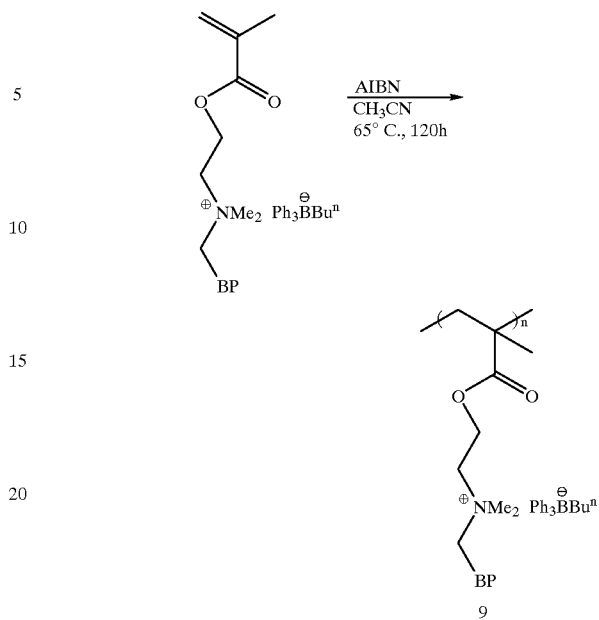

BP = C$_6$H$_4$-p-COC$_6$H$_5$

Photopolymers in accordance with the invention can be synthesized according to Scheme 3.

Scheme 3

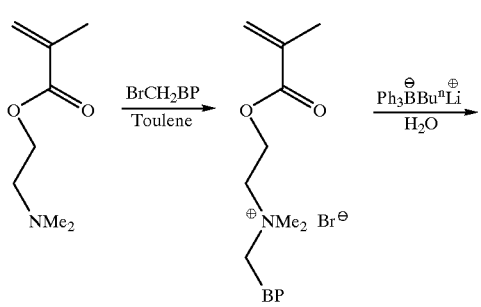

EXAMPLE 6

The following compounds were synthesized according to the following conditions:

Experimental procedure for N,N,N-tributyl-N-(p-benzoyl)benzyl ammonium triphenylbutyl borate (Compound 1).

Synthesis of N,N,N-tributyl-N-(p-benzoyl)benzyl ammonium bromide (Compound 2). 10.0 g (36.34 mmol) of 4-bromomethyl benzophenone was dissolved in ether-chloroform (2:1) mixture at room temperature. 8.76 g (47.26 mmol) of tributylamine was added into it and stirred at room temperature for 24 h while precipitate was formed. The precipitate was filtered and recrystalized from ethanol-ethylacetate (1:10) mixture. 11.70 g (70% yield) of white crystals was obtained: m.p. 160–161° C. $^1$H NMR (acetone, δ): 7.90 (m, 4H), 7.68 (m, 1H), 7.58 (m, 4H), 5.11 (s, 2H), 3.50 (m, 6H), 2.06 (m, 6H), 1.43 (m, 6H), 1.00 (t, J=7 Hz, 9H). Anal. Calcd. for C$_{26}$H$_{39}$BrNO: C, 67.86; H, 8.26; Br, 17.37. Found: C, 67.79; H, 8.28; Br, 17.43.

Synthesis of N,N,N-tributyl-N-(p-benzoyl)benzyl ammonium tetrafluroborate (Compound 3). 0.21 g (0.45 mmol) of benzophenone methyl tributylammonium bromide was dissolved in 10 mL water at 50–55° C. Undisolved dust materials were filtered out, if any present. 0.5 mL 48% by wt of fluoboric acid in water was added at 50° C. drop by drop with stirring. Precipitate was formed immediately. 10 mL water was added to it and stirred for 30 min. Product was filtered and washed with water. 0.16 g (80% yield) of white solid was obtained: m.p. 78–79° C. Anal. Calcd. for C$_{26}$H$_{39}$BF$_4$NO: C, 66.86; H, 8.14; Br, 0.0. Found: C, 66.93; H, 8.19; Br, 0.0.

Synthesis of N,N,N-tributyl-N-(p-benzoyl)benzyl ammonium triphenylbutyl borate (Compound 1).

Method A. 0.80 g (2.61 mm) of lithium triphenylbutyl borate was dissolved in 9 mL water and filtered out undissolved dust particles, if any. 1.22 g (2.65 mm) of benzophenone methyl tributylammonium bromide in 25 mL water-methanol (5:1) was added to borate solution drop by drop with stirring at room temperature. A white solid was formed immediately and stirring was continued for another 1 h after adding 25 mL water. White solid was filtered and dried overnight. After recrystallization from ethylacetate/ethanol. 1.20 g (68%) white crystals was obtained: m.p. 133–133.5° C. $^1$H NMR (acetone, δ): 7.92 (m, 2H), 7.80 (m, 4H), 7.68 (m, 1H), 7.59 (m, 2H), 4.73 (s, 2H, N—C$\underline{H}_2$—PH), 3.36 (m, 6H, N—C$\underline{H}_2$—CH$_2$), 1.95 (m, 6H, N—CH$_2$—C$\underline{H}_2$), 1.45 (m, 6H, N—C$_2$H$_4$—C$\underline{H}_2$), 1.23 (m, 2H, B—C$\underline{H}_2$), 1.02 (m, 13H, N—C$\underline{H}_3$ and B—CH$_2$—C$_2\underline{H}_4$), 0.77 (t, 3H, B—C$\underline{H}_3$). $^{11}$B NMR (DMSO): d –29.41. Anal. Calcd. for C$_{48}$H$_{62}$BNO: C, 84.87; H, 9.13; N, 2.06. Found: C, 84.93; H, 9.21; N, 2.00.
Method B. Tetramethyl ammonium triphenylbutyl borate was dissolved in hot acetone (50° C.). Undissolved or dust materials, if present, were filtered from the solution at 50° C. Solution of benzophenone methyl tributylammonium bromide (1.1 eq.) in acetone was added slowly with stirring at 50° C. While stirring, the reaction mixture became cloudy which indicated tetramethyl ammonium bromide was formed. After half an hour, a few mL of water was added to make the solution clear. After another 15–20 mins, water was slowly added with stirring while white solid formed. It was filtered, washed with water and dried (almost quantitative yield).

The photophysical properties of all three compounds (1–3) are determined by the benzophenone (BP) chromophore as can be seen from their absorption and emission spectra as shown in Table II. The absorption spectra of (1–3) above 300 nm are virtually identical and similar to BP absorption spectra. The n-π transition ($\lambda_{max}$=340 nm) is red shifted by ~5 nm but the absorption coefficient is also similar (68 ~200 1. mol$^{-1}$.cm$^{-1}$). The phosphorescence spectra [7° K in MeOH/EtOH (1:1)] are shifted 4 nm to the red relative to BP.

Time-resolved transient spectroscopy and steady-state photolysis were used to investigate the interaction mechanism in (1). Triplet decay rates were measured in acetonitrile (MeCN) and benzene using laser flash photolysis. While the quenching process in MeCN is found to be bimolecular from its concentration dependence, no triplet was detected in benzene. Under the same conditions, where no electron transfer is expected, the transient absorption of the triplet, (3) Table II, was detected in both solvents. This triplet absorbs similar to that of BP*$^3$ with $\lambda_{max}$=530 nm in MeCN and 540 nm in benzene. With bromide as the counter anion (2), the triplet lifetime was 60 nsec (Table II). These observations indicate that the triplet quenching in this system is an electron transfer process from the borate anion or bromide anion to BP*$^3$ in the benzophenonemethyl-tri-n-butyl ammonium cation. In the polar solvent MeCN (ε=36), (1) probably exists in the form of free ions and the electron transfer is an intermolecular process. Upon increasing the concentration, the triplet decay rate increases as a result of the intermolecular electron transfer quenching. The quenching rate constant is 1×10$^{10}$ M$^{-1}$S$^{-1}$ indicating a diffusion controlled process. Another indication for the intermolecular process in MeCN is that a mixture of compound (3), where no electron transfer occurs, with tetrabutylborate gave the same quenching rate constant. On the other hand, in the nonpolar solvent benzene (ε=2.3) where presumably (1) exists as a tight ion-pair, electron transfer is intramolecular process and too fast to measure on the nanosecond time scale.

TABLE II

Triplet Absorption Maximum and Lifetimes

| PBCH$_2$N + (C$_4$H$_9$)$_3$ X- | Solvent | Conc. (M/L)$^{a,b}$ | $\lambda_{max}$ (nm) | Triplet Lifetime ('10%) |
|---|---|---|---|---|
| (1) :X = BuB (Ph)$_3$ | PhH | <10$^{-4}$ | — | <10 ns |
| (2) :X = Br | PhH | <10$^{-4}$ | 540'5 | 60 ns |
| (3) :X = BF$_4$ | PhH | <10$^{-4}$ | 540'5 | 1.5 μs |

$^a$)Saturated solutions in benzene.
$^b$)Deaerated by bubbling with argon.

In an attempt to measure the intramolecular electron transfer in neat benzene a picosecond flash experiment was conducted. An immediate formation of a transient having $\lambda_{max}$=540 nm was observed. This produced absorbance signals of poor signal-to-noise ratio which precluded measurement of a precise lifetime. The best estimate was 300±150 ps. The addition of 1% (by volume) of MeCN to benzene caused the solubility to increase such that it was possible to obtain good kinetic data which led to the lifetime of the triplet in this solvent mixture of 1.2 nanoseconds (ns). It seems from these results that the triplet decay rate increases as the polarity of the solvent decreased. This, in turn, may reflect changes in the electron transfer rate constant.

The transient absorption spectra of the radical anions BP.$^-$ or MeBP.$^-$ with maxima around 720 nm was detected by photolysis of BP or MeBP in the presence of tetrabutylammonium triphenylbutyl borate salt. However, absorption in the spectral range for the expected analog radical (4) (all references are to Scheme 1 above) was not detected even in the polar solvent MeCN. In borate salts, it is known that back electron transfer is not significant since the boranyl radical, as it is produced, dissociates rapidly and irreversibly to give the alkyl radical and triphenylborane. The failure to observe (4) indicates that its life time is less than 10 nanoseconds and it dissociates or rearranges during the laser pulse.

Irradiation of (1) in MeCN gives p,p'-(dibenzoyl)bibenzyl (7) as the principle isolated product. This implicates the BPCH$_2$ radial is an intermediate most likely formed by the dissociation of (4) along with the tributylammonium radical cation, in the reaction pathway. In support of this, it was observed that a weak and broad absorption builds up with long life time around 380 nm in the transient absorption spectra. This absorption was assigned to the BPCH$_2$. radical in agreement with the reported absorption for benzyl radicals.

Based on the above observations, the mechanism proposed is that illustrated in Scheme I. Since the electron transfer is to the long lived triplet excited state, the relative contributions of intermolecular or intramolecular processes could be shown to depend on the polarity of the solvent.

EXAMPLE 7

The following polymers were synthesized taking advantage of the compounds and procedures below:

Homopolymer

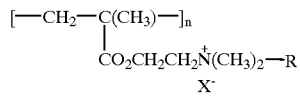

-continued

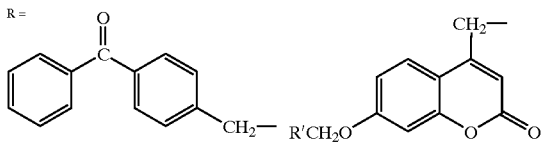

X = Ph₃B⁻Bu, Ph₄B⁻    R' = alkyl

Copolymers:

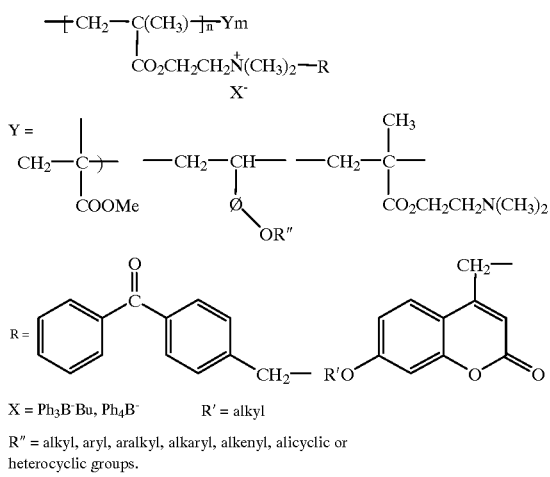

R" = alkyl, aryl, aralkyl, alkaryl, alkenyl, alicyclic or heterocyclic groups.

Synthesis 2-(Dimethylamino)ethyl butyrate. To a solution of N,N-dimethyl ethanolamine (4.45 g, 0.05 mol) in 140 mL of anhydrous tetrahydrofuran at room temperature under nitrogen was added triethylamine (5.05 g, 0.05 mol) and stirred for 15 min. The reaction mixture was then cooled at 0° C. and isobutyryl chloride (5.5 g, 0.05 mol) in 10 mL of tetrahydrofuran was added dropwise over 20 min. The resulting suspension was allowed to warm to room temperature and stirred overnight. The resulting solution was filtered and the solvent evaporated. The resulting product was then diluted by adding 200 mL of ether and subsequently washed with 10% aqueous NaOH solution, water and brine. After removal of the solvent, the crude product was chromatographed on a silica gel column using chloroform as the eluent to give liquid product (1.44 g, 50%). ¹H NMR (CDCl₃): δ 4.10 (t, J=5.82 Hz, 2H), 2.50 (m, 3H), 2.21 (s, 6H), 1.11 (s, 3H), 1.08 (s, 3H); MS m/z 159 (M⁺), 115, 71, 58 (100%), 42.

N,N-dimethyl-N-(p-benzoyl)benzyl-N-ethyl butyrate ammonium bromide. A solution of 2-dimethylamino ethylbutyrate (1.85 g, 11.60 mmol), and 4-(bromomethyl) benzophenone (3.18 g, 11.56 mmol) in acetone (50 mL) was stirred at room temperature for 24 hrs. The solvent was evaporated and the solid product dissolved in a minimum of chloroform. It precipitated when the solution was poured into ether (100 mL). The solid product was filtered, washed with ether, and dried under vacuum. After recrystallization from ethyl acetate/ethanol, the product was obtained as white needles (3.92 g, 80%); m.p. 152–54° C. ¹H NMR (CD₃CN): δ 7.80 (m, 4H), 7.67 (m, 1H), 7.55 (m, 4H), 4.98 (s, 2H), 4.58 (br s, 2H), 3.88 (m, 2H), 3.21 (s, 6H), 2.60 (m, 1H), 1.18 (s, 3H), 1.14 (s, 3H). Anal. Calcd. for $C_{22}H_{28}BrNO_3$: C, 60.86; H, 6.45; N, 3.22. Found: C, 60.62; H, 6.40; N, 3.16.

N,N-dimethyl-N-(p-benzoyl)benzyl-N-ethyl butyrate ammonium triphenylbutyl borate. N,N-dimethyl-N-(p-benzoyl)benzyl-N-ethyl butyrate ammonium bromide (1.0 g, 2.28 mmol) was dissolved in water (10 mL) and filtered. The lithium salt of triphenylbutyl borate (0.66 g, 2.15 mmol) in a minimum of water was added dropwise over 15 min. The solution was then diluted by adding water (75 mL), stirred for 15 min and filtered. The resulting solid was washed with water several times and dried under vacuum. The compound was obtained as white powder (1.18 g, 85%); m.p. 110–111° C. (ethyl acetate). ¹H NMR (CD₃CN): δ 7.83 (t, J=8.0 Hz, 4H), 7.70 (m, 1H), 7.59 (m, 4H), 7.26 (m, 6H), 6.96 (t, J=8.0 Hz, 7H), 6.79 (t, J=6.5 Hz, 3H), 4.51 (s, 2H), 4.49 (m, 2H), 3.65 (m, 2H), 2.94 (s, 6H), 2.62 (m, 1H), 1.93 (m, overlap with solvent peak, 2H, B—CH₂). 1.18 (s, 3H), 1.15 (s, 3H), 0.90 (m, 4H), 0.77 (t, J=6.5 Hz, 3H). Anal. Calcd. for $C_{44}H_{52}BNO_3$: C, 80.89, H, 7.96; N, 2.14. Found: C, 80.72; H, 7.93; N, 2.18.

N,N-dimethyl-N-(p-benzoyl)benzyl-N-ethyl methacrylate ammonium triphenyl butyl borate 11. Tetramethylammonium triphenylbutylborate (1.0 g, 2.68 mmol) was dissolved in 60 mL hot acetone (50° C.) and the resulting solution filtered. A solution of N,N-dimethyl-N-(p-benzoyl)benzyl-N-ethyl methacrylate ammonium bromide (1.16 g, 2.68 mmol) in minimum amount of hot acetone (with 1.0 mL methanol) was added dropwise. The reaction mixture became cloudy (due to formation of tetramethylammonium bromide) but it could be turned into clear solution upon addition of a few mL water. After stirring for 1 h at 45–50° C., product was precipitated by adding 100 mL water. The white product was filtered, washed with water several times, and dried under vacuum. The product was obtained as white semicrystals (1.50 g, 86%), m.p. 133–134° C. ¹H NMR (CD₃CN): δ 7.83 (m, 4H), 7.59 (m, 5H), 7.26 (br s, 6H), 6.96 (m, 6H), 6.83 (m, 3H), 6.14 (s, 1H), 5.74 (s, 1H), 4.53 (br s, 2H, CH₂—Ph), 4.46 (s, 2H, —O—CH₂), 3.58 (m, 2H, N—CH₂), 2.95 (s, 6H, N—CH₃), 1.94 (s, 3H), 1.23 (m, 2H, B—CH₂), 0.91 (m, 4H, B—CH₂—C₂H₄), 0.77 (t, J=7.0 Hz, 3H, B—CH₃). ¹¹B NMR (DMSO): δ -28.52. Anal. Calcd. for $C_{44}H_{40}BNO_3$: C, 81.14; H, 7.68; N, 2.15. Found: C, 81.06; H, 7.68; N, 2.12.

Typical Procedure for Radical Polymerization

A solution containing the desired amount of monomer (11) in anhydrous acetonitrile and 2,2'-azobis-isobutyronitrile, AIBN (3 mol % of total monomers) was charged into an oven dry polymerization tube. The polymerization tube was subjected to four freeze-pump-thaw cycles, sealed and heated at 60° C. for 120 hrs. The resulting reaction mixture was poured dropwise into a 20-fold excess diethyl ether. The polymer (Poly H1) was collected by filtration and purified by reprecipitation from acetonitrile in diethyl ether and methanol. The same procedure was repeated with a charge of 50% 11 and 50% MMA to obtain Poly CP1 and a charge of 20% 11 with 80% MMA to obtain Poly CP2.

Homopolymer, Poly H1. 70% yield by wt.; ¹H NMR (CD₃CN): δ 7.38–7.80 (br m, 9H, benzophenone gr), 7.28 (m, 6H, aromatic), 6.95 (m, 6H, aromatic), 6.78 (m, 3H, aromatic), 4.39 (br, 2H, Ph—CH₂), 3.39 (m, 2H, O—CH₂), 2.88 (br, 2H, CH₂—N), 2.16 (s, 6H), 1.93 (m, 3H, x-methyl), 1.16 (m, 2H, B—CH₂), 0.90 (m, 4H), 0.73 (t, J=7.0 Hz, 3H). Anal. Calcd. for $C_{44}H_{40}BNO_3$: C, 81.14; H, 7.68; N, 2.15. Found: C, 80.45; H, 7.60; N, 2.51.

Copolymer 1; Poly CP1. 76% yield by wt.; ¹H NMR (CD₃CN): δ 7.40–7.88 (m, 9H, benzophenone gr), 7.30 (m, 6H), 6.92 (m, 6H), 6.86 (m, 3H), 4.22 (br, 2H, Ph—CH₂), 3.40–3.50 (br, 5H, O—C₂ and O—CH₃), 2.70 (br, 2H, CH₂—N), 2.14 (s, 6H), 1.94 (m, 6H, two x-methyl gr), 1.20 (m, 2H), 0.92 (m, 4H), 0.78 (t, J=7.0 Hz 3H). Anal. Calcd. for $(C_{44}H_{50}BNO_3)$ 0.50 $(C_5H_8O_2)$ 0.50: C, 78.33; H, 7.72; N, 1.86. Found: C, 77.54; H, 7.76; N, 1.78.

Copolymer 2, Poly CP2. 73% yield by wt.; $^1$H NMR (CD$_3$CN): δ 7.45–7.95 (m, 9H, benzophenone moiety), 7.28 (m, 6H, aromatic), 6.98 (m, 6H, aromatic), 6.82 (m, 3H, aromatic), 4.40 (br, 2H, Ph—C$\underline{H}_2$), 3.56 (s, 5H, O—C$\underline{H}_2$ and O—C$\underline{H}_3$ of MMA), 2.90 (br s, 2H, N—C$\underline{H}_2$), 2.18 (s, 6H), 1.98 (m, 6H), 1.24 (m, 2H), 0.95 (m, 4H), 0.80 (m, 3H). Anal. Calc. for (C$_{44}$H$_{50}$BNO$_3$)0.20 (C$_5$H$_8$O$_2$)0.80: C, 73.10; H, 7.80; N, 1.33. Found: C, 73.04; H, 7.86; N, 1.4.

Photoinitiating activity measurement. A calculated amount of photoinitiator was added to the bifunctional acrylic monomer, diethylene glycol diacrylate and stirred for several hours to form a homogenous solution. (In some cases we needed to stir at 60° C.). A few drops of the formed solution was placed between regular NaCl plates using a 15 micron thick teflon spacer and cured using a high pressure Hg arc lamp (200 W) as the light source. A cutoff filter that allowed only the narrow band at 365 nm to penetrate the sample was used. Double bond conversion (DC) (acrylate to polyacrylate) was monitored by observing the disappearance of the absorption peak at 810 cm$^{-1}$ due to C=C of acrylate in the FTIR according to the following formula:

$$DC = (X_0 - X_i/X_0) \times 100\%$$

where X is the absorption at 810 cm$^{-1}$ and X$_0$ is the absorption at t=0; X$_i$ is the absorption at time t=t.

Having described the invention in detail and by reference to preferred embodiments thereof, it will be apparent that modification and variations are possible without departing from the scope of the invention defined in the appended claims.

What is claimed is:

1. A compound of the formula

A-L$^+$D$^-$ where A is a moiety which absorbs radiation and enters an excited state in which it accepts an electron; L is a linking group which tethers an electron acceptor moiety A to the electron donor moiety D$^-$; and D$^-$ is a moiety represented by the formula (V):

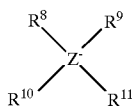

where Z is an element selected from the group consisting of boron, aluminum and gallium and R$^8$, R$^9$, R$^{10}$ and R$^{11}$ are independently selected from the group consisting of alkyl, aryl, alkaryl, aralkyl, alkenyl, alkynyl, alicyclic, heterocyclic and a cyclic group wherein at least two of the R$^8$, R$^9$, R$^{10}$ and R$^{11}$ may combine to form a cyclic group, wherein said moiety D$^-$ donates an electron to the excited state of the A moiety and releases a free radical; and L$^+$ is a cationic linking group of the formula

-L'-G- where L' is a moiety which forms a stable radical with the acceptor moiety A upon transfer of an electron from the donor moiety D$^-$ to the acceptor moiety A and G is moiety which forms a leaving group upon said transfer and is selected from the group consisting of ammonium, phosphonium, arsonium, antimonium, sulfonium, oxonomium, thioxonium, halonium and polyvalent metal cation.

2. The compound of claim 1 wherein L$^+$ has the formula -L'-G- where L' is a moiety selected from the group consisting of

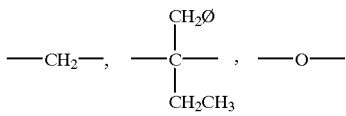

and —S—; and G is a moiety selected from the group consisting of ammonium, phosphonium, arsonium, antimonium, sulfonium, oxonomium, thioxonium, halonium and polyvalent metal cation which forms a leaving group upon electron transfer from said donor moiety D to said electron acceptor moiety A.

3. The compound of claim 2 wherein G is ammonium having the formula N$^+$R$_3$, wherein R is the same or different and represents hydrogen, alkyl, or a moiety selected from the group consisting of polyacrylates, polyacrylate copolymers, novolak resins, polystyrenes, and polystyrene copolymers.

4. The compound of claim 2 wherein the compound is represented by the formula (IIA)

A[L']N$^+$R$_3$D$^-$         (IIA)

where L' is selected from the group consisting of

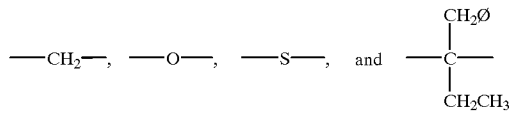

R is the same or different and represents hydrogen, alkyl, aralkyl or a higher molecular weight moiety selected from the group consisting of a poly- or copolyacrylate, a poly- or copolymethacrylate, a novolak resin, and a poly- or copolystyrene; and A and D are defined as in claim 1.

5. The compound of claim 1 wherein said electron acceptor moiety A is selected from a group consisting of aromatic ketones, oximinoketones, quinones, keto dyes, acetophenone acetals, benzoin ethers, cyanine dyes, merocyanine dyes, merostyryl dyes, xanthene dyes, oxonal dyes, hemioxonal dyes, polycyclic aromatic hydrocarbons, halonium salts, and sulfonium salts.

6. The compound of claim 5 wherein said electron acceptor moiety is an aromatic ketone selected from the group consisting of benzophenones, acetophenones, xanthones and thioxanthones.

7. The compound of claim 6 wherein said aromatic ketone is selected from the group consisting of benzophenone, substituted benzophenones, acetophenone, substituted acetophenones, wherein said substituted benzophenones and said substituted acetophenones are substituted by a member selected from the group consisting of —CH$_3$, —OH, —Br, —Cl, —OR and —NR$_2$ where R is alkyl or aryl.

8. The compound of claim 7 wherein said aromatic ketone moiety is benzophenone.

9. The compound of claim 5 wherein said electron acceptor is a coumarin.

10. The compound of claim 9 wherein said coumarin is substituted by a member selected from the group consisting of —OR and —NR$_2$, where R is alkyl.

11. The compound of claim 1 wherein Z is boron.

12. The compound of claim 1 wherein D$^-$ is an organoborate moiety selected from a tetraalkylborate, a tetraarylborate, a triarylalkylborate, a aryltrialkylborate, or a diaryldialkyborate.

13. The compound of claim 12 wherein said organoborate moiety is a triarylalkylborate.

14. The compound of claim 13 wherein said organoborate moiety is a triphenyl-n-butylborate.

15. The compound of claim 14 wherein said compound is N-p-benzoylbenzyl N,N,N-tributylammonium triphenylbutylborate.

16. The compound of claim 1 wherein G is ammonium.

17. The compound of claim 1 wherein A is a substituted or unsubstituted benzophenone or a substituted or unsubstituted coumarin.

18. The compound of claim 17 wherein L' is selected from the group consisting of

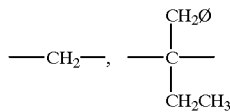

19. A compound of the formula (III):

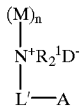

where M is a moiety derived from polymerization of one or more monomers, $R^1$ is hydrogen or an alkyl group having 1 to 6 carbon atoms, n is about 10 to 20, A is a moiety which absorbs radiation and enters an excited state in which it accepts an electron, D is a moiety which donates an electron to the excited state of the A moiety and L' is a moiety which yields a stable radical upon electron transfer.

20. A compound of the formula $A-L'-N^+R'_3D^-$ where A is benzophenone or a benzophenone substituted by a member of the group consisting of —$CH_3$, —OH, Br, Cl, —OR, and —$NR_2$ where R is alkyl or aryl; or a coumarin or a coumarin substituted by a member of the group consisting of —$NR_2$ and —OR where R is an alkyl; L' is a moiety selected from the group

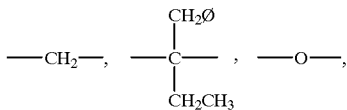

and —S—; R' is hydrogen, alkyl or a poly- or copolyacrylate, a poly- or copolymethacrylate, a novolak resin, or a poly- or copolystyrene; and D is represented by the formula:

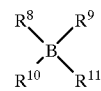

where $R^8$, $R^9$, $R^{10}$ and $R^{11}$ are independently selected from the group consisting of alkyl, aryl, alkaryl, aralkyl, alkenyl, alkynyl, alicyclic, heterocyclic and a cyclic group wherein at least two of the $R^8$, $R^9$, $R^{10}$ and $R^{11}$ may combine to form a cyclic group.

* * * * *

UNITED STATES PATENT AND TRADEMARK OFFICE
CERTIFICATE OF CORRECTION

PATENT NO. : 5,998,496
DATED : December 7, 1999
INVENTOR(S) : Hassoon et al.

It is certified that error appears in the above-identified patent and that said Letters Patent is hereby corrected as shown below:

Title Page: Item [75], the Inventors should read: Salah A. Hassoon; Ananda M. Sarker, both of Bowling Green, Ohio; Douglas C. Neckers, Perrysburg, Ohio; Alexandre Mejiritski, Bowling Green, Ohio; Adrian Lungu, Old Bridge, New Jersey; Alexander Y. Polykarpov, Mason, Ohio Claim 4, col. 22, line 24, after (IIA) insert --: --.

Signed and Sealed this

Fifth Day of September, 2000

Attest:

Q. TODD DICKINSON

*Attesting Officer*

*Director of Patents and Trademarks*